United States Patent [19]

Klaveness et al.

[11] Patent Number: 5,567,412
[45] Date of Patent: Oct. 22, 1996

[54] CONTRAST AGENTS CONSISTING OF GALACTOSE PARTICLES AND AN AMPHILIC CARBOXYLIC ACID

[75] Inventors: Jo Klaveness, Oslo; Pål Rongved, Hellvik, Norway; Lars Stubberud, Södertälje, Sweden

[73] Assignee: Nycomed Imaging AS, Oslo, Norway

[21] Appl. No.: 256,150

[22] PCT Filed: Jan. 8, 1993

[86] PCT No.: PCT/EP93/00026

§ 371 Date: Sep. 29, 1994

§ 102(e) Date: Sep. 29, 1994

[87] PCT Pub. No.: WO93/13802

PCT Pub. Date: Jul. 22, 1993

[30] Foreign Application Priority Data

Jan. 9, 1992 [GB] United Kingdom ............. 9200387

[51] Int. Cl.⁶ ......................................... A61K 49/00
[52] U.S. Cl. ...................... 424/9.35; 424/9.5; 424/9.51; 424/9.52
[58] Field of Search ...................... 424/9.5, 9.51, 424/9.52, 9.35

[56] References Cited

U.S. PATENT DOCUMENTS

| | | | |
|---|---|---|---|
| 4,657,756 | 4/1987 | Rasor et al. | 424/9 |
| 5,141,738 | 8/1992 | Rasor et al. | 424/2 |

FOREIGN PATENT DOCUMENTS

| | | |
|---|---|---|
| 0123235 | 10/1984 | European Pat. Off. |
| 0365467 | 4/1990 | European Pat. Off. |

OTHER PUBLICATIONS

Schlief et al., *Invest. Radiol.*, 26, suppl. 1, pp. S–188–9 and discussion S198–200, 1991.

*Primary Examiner*—Richard L. Raymond
*Assistant Examiner*—Mary C. Cebulak
*Attorney, Agent, or Firm*—Bacon & Thomas

[57] ABSTRACT

The present invention relates to contrast agents comprising microbubble-generating carbohydrate microparticles in admixture with an amphiphilic organic acid containing in excess of 20 carbon atoms. The contrast agents exhibit good stability and/or enhanced contrast effect and may be used in diagnostic applications such as ultrasound and MR imaging.

12 Claims, 2 Drawing Sheets

CONTRAST AGENTS CONSISTING OF GALACTOSE PARTICLES AND AN AMPHILIC CARBOXYLIC ACID

This application is a 371 of PCT/EP93/00026 filed Jan. 8, 1993.

This invention relates to novel contrast agents, more particularly to new microparticulate contrast agents of use in diagnostic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas microbubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas microbubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of generating and/or stabilising gas microbubbles for echocardiography and other ultrasonic studies, for example using emulsifiers, oils, thickeners or sugars.

Techniques involving the use of sugars in ultrasound contrast agents are described in, for example, U.S. Pat. No. 4,681,119, U.S. Pat. No. 4,442,843 and U.S. Pat. No. 4,657,756, which disclose the use of particulate solids having a plurality of gas-filled voids and preferably also a plurality of nuclei for microbubble formation. EP-A-0123235 and EP-A-0122624 suggest ultrasound contrast agents consisting of surfactant-coated or surfactant-containing gas-containing microparticles which may include a variety of sugars. DE-A-3834705 proposes the use of suspensions containing microparticles of mixtures of at least one $C_{10-20}$ fatty acid with at least one non-surface active substance, including sugars such as cyclodextrins, monosaccharides, disaccharides or trisaccharides, as well as other polyols and inorganic and organic salts. One material of this type, SHU 508 (Levovist®), is described in the following publications: Schlief, R. et al., *Circulation Supplement III* (1990) 82, p. 28; Schartl, M. et al., *Circulation Supplement III* (1990) 82, p. 261; Fritzsch, T. et al., *Invest. Radiol.* (1990) 25 (Suppl), pp. 160–161; Schlief, R. et al., *Echocardiography* (1990) 7, pp. 61–64; Loughery, E. J. et al., *Echocardiography* (1990) 7, pp. 279–292; and Smith, M. D. et al., *JACC* (1989) 13, pp. 1622–1628.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents.

A general disadvantage of existing gas-containing/gas-generating particulate contrast agents such as the sugar-based agents discussed above is their relative lack of stability in vivo. This is a particular problem in applications such as echocardiography, where there is a need for improved contrast agents combining sufficient stability and small microbubble size (typically less than about 10 μm, preferably less than about 7 μm) to permit passage through the pulmonary capillary bed and so allow enhanced visualisation of the left side of the heart, preferably for more than one passage of circulation. Thus while previously proposed agents such as the above-described SHU 508 have been found to permit some visualisation of the left side of the heart, their attenuative effect on ultrasound signals is comparatively short-lived, e.g. as evidenced by half lives in vitro of less than one minute. There is accordingly a need for contrast agents which generate microbubble systems exhibiting greater stability while still providing a high level of contrast efficiency.

The present invention is based on our finding that contrast agents comprising microparticles of a carbohydrate admixed with an amphiphilic organic acid containing in excess of 20 carbon atoms may be used to generate microbubble systems exhibiting substantially enhanced stability and/or contrast effect relative to previously proposed carbohydrate-based contrast agents. In the ultrasound field this may be demonstrated by, for example, in vitro measurements of initial attenuation levels and the half lives of the attenuative effect; a useful indication of the combined effect of these properties is the integral obtained by determining the area under the curve of a plot of attenuation against time.

Figure 1:
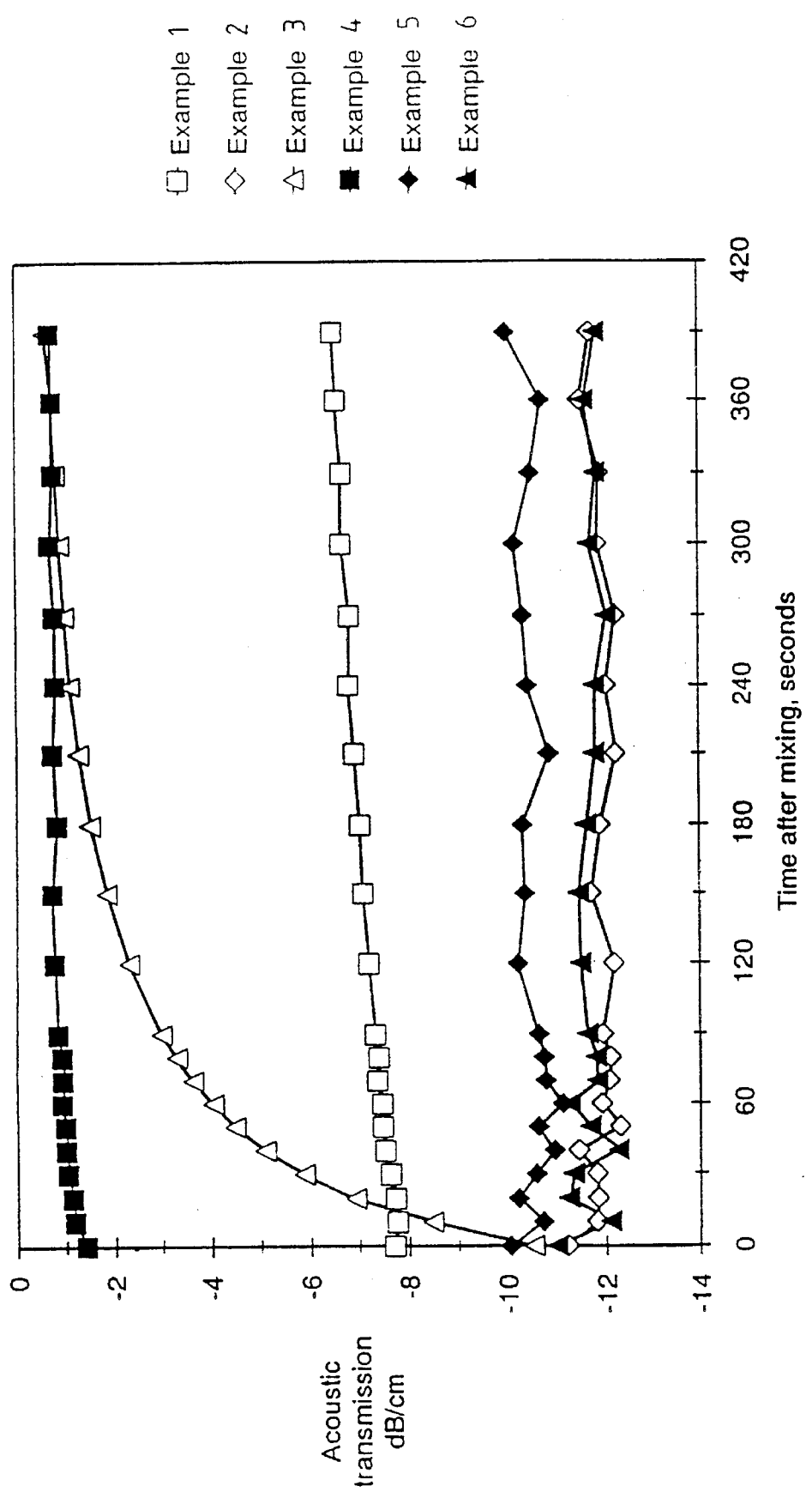
FIGS. 1 and 2 show the acoustic transmission for the exemplified products plotted against time.

Thus, according to one aspect of the present invention, there are provided contrast agents comprising microbubble-generating carbohydrate microparticles in admixture with an amphiphilic organic acid containing in excess of 20 carbon atoms.

The microparticulate carbohydrate is preferably water soluble, and may for example be selected from hexoses such as glucose, fructose or galactose; disaccharides such as sucrose, lactose or maltose; pentoses such as arabinose, xylose or ribose; and α-, β- and γ-cyclodextrins; the term "carbohydrate" as used herein is also intended to embrace sugar alcohols, e.g. alditols such as mannitol or sorbitol. Microparticles of the above carbohydrates will normally have gas present as an inclusion in the voids of their crystal structure and/or adhered to their surface, which gas may generate microbubbles when, for example, the microparticles are suspended or dissolved in an injectable carrier liquid, for example water for injection, an aqueous solution of one or more inorganic salts (e.g. physiological saline or a physiological buffer solution), an aqueous solution of a monosaccharide (e.g. glucose or galactose) or disaccharide (e.g. lactose), or an aqueous solution of a physiologically tolerable monohydric or polyhydric alcohol (e.g. ethanol, propanol, isopropanol, ethylene glycol, propylene glycol, glycerine or polyethylene glycol).

In addition to or alternatively to air, any biocompatible gas may be employed in the contrast agents of the invention, for example nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The term "gas" as used herein includes any substance in the gaseous form at 37° C. The gas may be contained in the contrast agent in such a way that before use the product is non-contrast giving but becomes effective on administration, e.g. as a result of the gas forming microbubbles as a soluble carbohydrate matrix dissolves.

Additionally or alternatively the carbohydrate may incorporate one or more gas precursors, including carbonates and bicarbonates (e.g. sodium or ammonium bicarbonate) and aminomalonate esters.

The amphiphilic organic acids in contrast agents according to the invention should contain in excess of 20 carbon atoms and preferably contain not more than 50 carbon atoms; acids containing 22–40, typically 22–30, carbon atoms may thus conveniently be employed. The acids preferably contain at least one carboxyl group which may, for example, be attached to an aliphatic group (e.g. as in straight chain saturated fatty acids such as behenic, lignoceric, cerotic or melissic acid; or straight chain unsaturated fatty acids such as cetoleic, erucic, brassidic or selacholeic acid or a polyunsaturated acid such as 10,12-tricosadiynoic acid), to a monocyclic or polycyclic cycloaliphatic group (as in amphiphilic steroids such as cholanic acid), or to a monocyclic or polycyclic aromatic or araliphatic group.

The amphiphilic organic acid may, for example, be present in an amount of 0.01–5.0 wt. %, preferably 0.1–2.0 wt. %, relative to the microparticulate carbohydrate.

The contrast agents of the invention may be used in a variety of diagnostic imaging techniques, including ultrasound, MR and X-ray imaging. Their use in diagnostic ultrasonic imaging and MR imaging, e.g. as susceptibility contrast agents, constitute preferred features of the invention.

The contrast agents of the invention may be prepared by any convenient method which leads to physical admixture of the carbohydrate and amphiphilic organic acid and to production of microparticles of the desired size.

In one preferred method according to the invention the carbohydrate and the amphiphilic acid are each dissolved in appropriate mutually miscible solvents (e.g. water in the case of the carbohydrate and a lower alkanol such as ethanol in the case of the amphiphilic acid), the resulting solutions are mixed, the solvents are removed (e.g. by evaporation under reduced pressure), and the resulting solid mixture is micronised to yield the desired microparticles. It will be appreciated that all such operations should be effected under sterile conditions.

Conventional micronisation techniques such as grinding or milling may be employed. Ball-milling of the solid mixture has been found to be particularly advantageous, permitting the preparation of microparticles in the form of aggregates (for example having an aggregate size of 20–125 micrometers, such as 30–50 micrometers) of particles having a particle size of, for example, 1–50 micrometers, such as 1–10 micrometers. Such aggregates will tend to contain a substantial volume of air adsorbed on their surfaces and entrained in voids such as interparticle cavities or at grain boundaries between the crystallites. The particle size may, for example, be selected to be substantially commensurate with the desired microbubble size. In ultrasonic applications such as echocardiography, in order to permit free passage through the pulmonary system and to achieve resonance with the preferred imaging frequencies of about 0.1–15 MHz, it may be convenient to employ microbubbles and microparticles having an average size of 0.1–10 μm, e.g. 1–7 μm; the use of microparticles of average size 1–4 μm to generate microbubbles with an average size of 4–7 μm is generally advantageous. Substantially larger bubbles and particles, e.g. with average sizes up to 500 μm, may however be useful in other applications, for example gastrointestinal imaging.

The following non-limitative Examples serve to illustrate the invention:

EXAMPLES 1–9

General Procedure

D-(+)-galactose (10.0 g) was dissolved in distilled water (14.2 g) at 50° C., sterile filtered and cooled on ice to a temperature of 4°–8° C. The stated amounts of the amphiphilic acids listed in Table 1 were each dissolved in the amount of 96% ethanol shown in the Table, at 50°–78° C., and the resulting solution was sterile filtered and then aseptically added to the cold aqueous galactose solution under stirring. The resulting mixture was evaporated to dryness under reduced pressure (10 torr, 40° C.), and the resulting solid product was dried in a desiccator overnight and then ground for 10 minutes under aseptic conditions in a stainless steel ball mill having a 50 ml grinding cup and 3×20 mm balls (Retsch centrifugal ball mill, S1). The ground product was dried in a desiccator for 24 hours.

TABLE 1

| Example No. | Amphiphilic acid | Amount of acid (% w/w relative to galactose) | Amount of ethanol (g) |
| --- | --- | --- | --- |
| 1 | Behenic acid | 0.1 | 1.2 |
| 2 | " | 1.0 | 1.2 |
| 3 | 10,12-tricosadiynoic acid | 0.2 | 3.5 |
| 4 | Melissic acid | 0.01 | 0.8 |
| 5 | " | 0.1 | 1.2 |
| 6 | " | 1.0 | 3.28 |
| 7 | 5β-cholanic acid | 0.01 | 1.2 |
| 8 | " | 0.1 | 1.2 |
| 9 | " | 1.0 | 4.0 |

EXAMPLE 10

Echogenicity in Vitro 10 ml of propylene glycol mixed with 90 ml of 5% dextrose in water was used as a carrier liquid for determining the echogenicity of the products of Examples 1–9. 1.0 g of each product was dispersed in 3.0 ml of the carrier liquid and shaken for 15 seconds. The resulting mixture was added to 52 ml of 5% human serum albumin infusion solution in the measurement cell and the acoustic effects of the products were investigated by measuring the acoustic transmission through the samples using a 5 MHz broadband transducer in a pulse-reflection technique. The temperature in the measurement cell was stabilised to 37° C. and circulation of the liquid was maintained by means of stirring at a constant rate. Ultrasound transmission through the samples was measured as a function of time over a duration of 390 seconds. Results were normalized to measurements on a reference consisting of 55 ml of 5% human serum albumin infusion solution.

Figure 2:
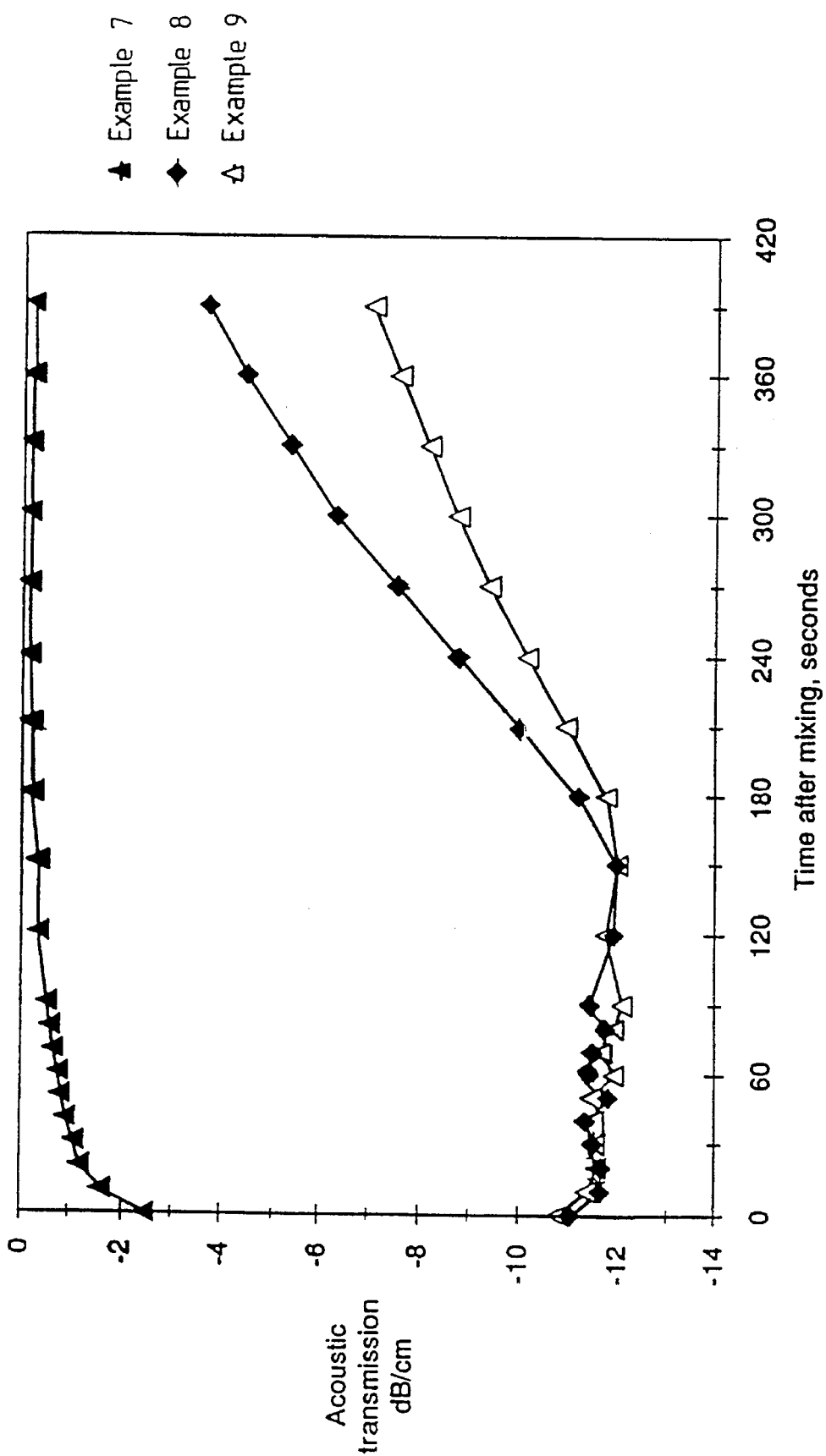

Results for the exemplified products are shown in FIGS. 1 and 2 of the accompanying drawings. It will be apparent that the majority of the products exhibit a strong effect on ultrasonic attenuation in vitro, an effect which in most cases persisted for several minutes. A number of products showed no significant decrease in attenuation over the duration of measurement.

EXAMPLE 11

Particle Size Analysis

The particle size distribution of the product of Example 8 was analysed using a Coulter LS 100 light scatter apparatus. Approximately 2 g of this product were fed to the analyser using a vibrating screen. The particle size distribution was as follows:

| Accumulated Vol % < | 10 | 25 | 50 | 75 | 90 |
|---|---|---|---|---|---|
| Size (μm) | 0.509 | 0.716 | 2.103 | 3.311 | 4.408 |
| Mean diameter: 2.2 μm | | Median diameter: 2.1 μm | | | |

We claim:

1. A contrast agent comprising microbubble-generating carbohydrate microparticles in admixture with an amphiphilic $C_{22-50}$ organic acid.

2. A contrast agent as claimed in claim 1 in which the carbohydrate is a water-soluble pentose, hexose, disaccharide, cyclodextrin or sugar alcohol.

3. A contrast agent as claimed in claim 2 in which the carbohydrate is galactose.

4. A contrast agent as claimed in claim 1 in which the amphiphilic organic acid is an aliphatic, cycloaliphatic, araliphatic or aromatic carboxylic acid.

5. A contrast agent as claimed in claim 4 wherein the amphiphilic organic acid is a $C_{22-30}$ straight chain saturated fatty acid.

6. A contrast agent as claimed in claim 1 in which the amphiphilic organic acid is present in an amount of 0.1–2.0% w/w relative to the carbohydrate.

7. A contrast agent as claimed in claim 1 in which the microparticles are aggregates having an aggregate size of 30–50 micrometers of microparticles having a particle size of 1–10 micrometers.

8. A process for preparing a contrast agent as claimed in claim 1 which comprises mixing solutions of the carbohydrate and the amphiphilic organic acid in appropriate mutually miscible solvents, removing said solvents, and micronising the resulting solid mixture to yield the desired microparticles.

9. A process as claimed in claim 8 in which the solid mixture is micronised by ball-milling.

10. A method of generating an enhanced diagnostic image of a human or non-human animal body comprising administering into the vascular system of said body a diagnostic image enhancing amount of a contrast agent according to claim 1.

11. A method of generating an enhanced diagnostic ultrasonic image of a human or non-human animal body comprising administering into the vascular system of said body a diagnostic ultrasonic image enhancing amount of a contrast agent according to claim 1.

12. A method of generating an enhanced magnetic resonance image of a human or non-human animal body comprising administering to said body a magnetic resonance image enhancing amount of a contrast agent according to claim 1.

* * * * *